US010059653B2

(12) United States Patent
Bertolini et al.

(10) Patent No.: US 10,059,653 B2
(45) Date of Patent: Aug. 28, 2018

(54) PROCESS FOR THE PREPARATION OF INDANAMINE DERIVATIVES AND NEW SYNTHESIS INTERMEDIATES

(71) Applicant: LABORATORIO CHIMICO INTERNAZIONALE S.P.A., Milan MI (IT)

(72) Inventors: Giorgio Bertolini, Rodano (IT); Paolangelo Cerea, Rodano (IT); Corrado Colli, Rodano (IT); Lazzaro Feliciani, Rodano (IT); Federico Gassa, Rodano (IT); Aldo Bianchi, Solaro (IT); Federica Colombo, Milan (IT); Stefano Maiorana, Milan (IT); Filippo Nisic, Milan (IT)

(73) Assignee: OLON S.P.A., Rodano (MI) (IT)

( * ) Notice: Subject to any disclaimer, the term of this patent is extended or adjusted under 35 U.S.C. 154(b) by 0 days.

(21) Appl. No.: 15/541,931

(22) PCT Filed: Jan. 19, 2016

(86) PCT No.: PCT/IB2016/050249
§ 371 (c)(1),
(2) Date: Jul. 6, 2017

(87) PCT Pub. No.: WO2016/116857
PCT Pub. Date: Jul. 28, 2016

(65) Prior Publication Data
US 2017/0362161 A1    Dec. 21, 2017

(30) Foreign Application Priority Data
Jan. 20, 2015   (IT) .............................. MI2015A0045

(51) Int. Cl.
| C07C 209/22 | (2006.01) |
| C07C 67/00 | (2006.01) |
| C07C 45/46 | (2006.01) |
| C07C 29/00 | (2006.01) |
| C07C 303/28 | (2006.01) |
| C07C 69/14 | (2006.01) |
| C07C 69/78 | (2006.01) |
| C07C 35/32 | (2006.01) |
| C07C 309/73 | (2006.01) |
| C07C 309/66 | (2006.01) |
| C07C 49/84 | (2006.01) |

(52) U.S. Cl.
CPC ............ *C07C 209/22* (2013.01); *C07C 29/00* (2013.01); *C07C 35/32* (2013.01); *C07C 45/46* (2013.01); *C07C 49/84* (2013.01); *C07C 67/00* (2013.01); *C07C 69/14* (2013.01); *C07C 69/78* (2013.01); *C07C 303/28* (2013.01); *C07C 309/66* (2013.01); *C07C 309/73* (2013.01); *C07C 2602/08* (2017.05)

(58) Field of Classification Search
None
See application file for complete search history.

(56) References Cited

FOREIGN PATENT DOCUMENTS

| CN | 103360264 B | 11/2014 |
| WO | 00/75114 A1 | 9/2000 |
| WO | 03/076387 A2 | 9/2003 |
| WO | 2013/132514 A2 | 9/2013 |

OTHER PUBLICATIONS

Prashad M., et al., An Efficient and Economical Synthesis . . . , Organic Process Research and Development, vol. 10, No. 13, pp. 135-141, 2006.
International Search Report and Written Opinion for International Application No. PCT/IB2016/050249 (15 Pages) (dated Apr. 25, 2016).

*Primary Examiner* — Clinton A Brooks
(74) *Attorney, Agent, or Firm* — Lucas & Mercanti, LLP

(57) ABSTRACT

Subject-matter of the invention is a process for the preparation of a key intermediate in the synthesis of indacaterol. Subject-matter of the invention are also new synthesis intermediates. Formula (I):

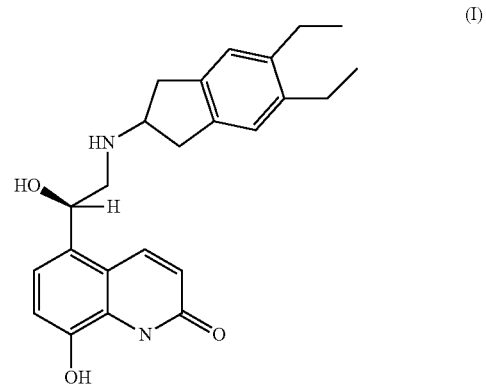

16 Claims, No Drawings

PROCESS FOR THE PREPARATION OF INDANAMINE DERIVATIVES AND NEW SYNTHESIS INTERMEDIATES

CROSS-REFERENCE TO RELATED APPLICATIONS

This application is a 371 of PCT/IB2016/050249 filed Jan. 19, 2016, which claims the benefit of Italian Patent Application No. MI2015A000045 filed Jan. 20, 2015.

BACKGROUND OF THE INVENTION

Indacaterol is the international nonproprietary name of the compound (R)-5-[2-[(5,6-diethyl-2,3-dihydro-1H-inden-2-yl)amino]-1-hydroxyethyl]-8-hydroxyquinolin-2(1H)-one, having the following formula:

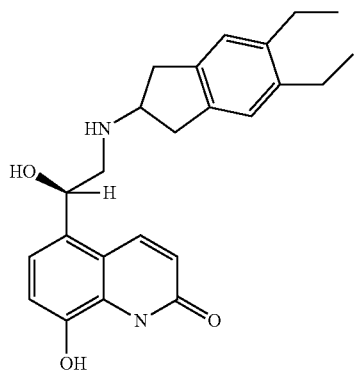 [SMILES: CCc1cc2c(cc1CC)CC(NC[C@@H](O)c1ccc(O)c3[nH]c(=O)ccc13)C2]

Indacaterol is a drug acting as selective agonist of beta-2 receptors and is recommended in the bronchospasm and in other bronchial pathological conditions such as bronchial asthma and chronic obstructive pulmonary disease.

Some synthesis of the indacaterol are known which make use of 4,5-diethyl-1H-inden-2-yl-amine with the following formula

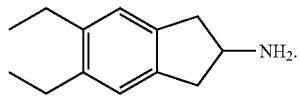

or N-substituted derivatives thereof, in particular the N-benzyl derivative, as key intermediates. Said intermediates are usually produced starting from the indanamine after protection of the amine group. For example, WO03/076387 describes the preparation of 4,5-diethyl-1H-inden-2-yl-amine starting from the indanamine protected with trifluoroacetyl, by means of two consecutive Friedel-Crafts reactions, each of them followed by the reduction of the introduced ketone group. The above indicated process has the drawback of requiring the isolation and purification of the compounds obtained after each individual reaction step, thus resulting in a process complexity related to the several isolations of the intermediates and, obviously, in a yield loss.

Moreover, the preparation of the derivative wherein R is a benzyl group is described starting from the 4,5-diethyl-1H-inden-2-yl-amine, whose amine group is reacted with benzyl chloride and then subjected to reduction, according to the following scheme:

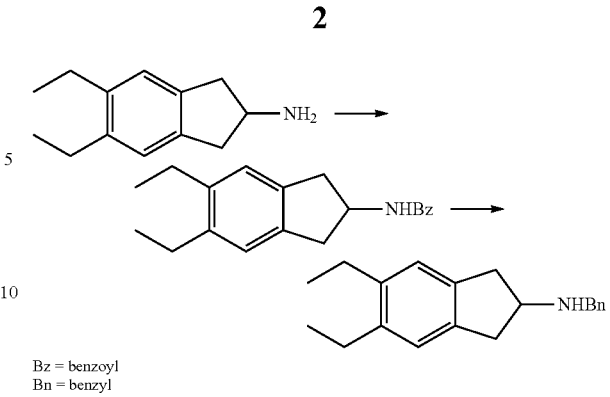

Bz = benzoyl
Bn = benzyl

As it can be noted, the preparation of the benzyl derivative reported above requires two additional reaction steps, which affect the economy of the synthesis and determines higher costs, in particular in the case of industrial production.

WO 00/75114 describes the preparation of 4,5-diethyl-1H-inden-2-yl-amine starting from diethylbenzene; the process results in very low yields and, in addition, the starting compound (diethylbenzene) is particularly expensive. These drawbacks make the process described in WO00/75114 of no industrial interest.

Therefore, there is the need of finding a synthesis of the compounds of formula (I) which is of simple realization and does not require complex isolation and purification steps of the intermediates.

OBJECTS OF THE INVENTION

It is an object of the present invention to provide a process for the preparation of 4,5-diethyl-1H-inden-2-yl-amine or a N-derivative thereof which provides excellent yields and purity, while not necessarily requiring the isolation and purification of all the intermediate compounds.

It is another object of the invention to provide new versatile intermediate derivatives that can be used in the preparation of 4,5-diethyl-1H-inden-2-yl-amine or an N-derivative thereof, or as intermediates in the synthesis of other chemical compounds.

DESCRIPTION OF THE INVENTION

It has been found that it is possible to prepare the 4,5-diethyl-1H-inden-2-yl-amine or the N-derivatives thereof or the salts thereof, by means of a simple synthesis starting from the indanol.

Therefore, according to one of its aspects, subject-matter of the invention is a process for the preparation of a compound of formula (I)

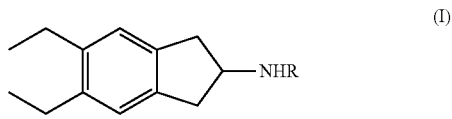

(I)

or salts thereof, wherein R is a hydrogen atom or an amine protecting or activating group, comprising the following steps from (a) to (g) according to the following scheme (I):

Scheme (I)

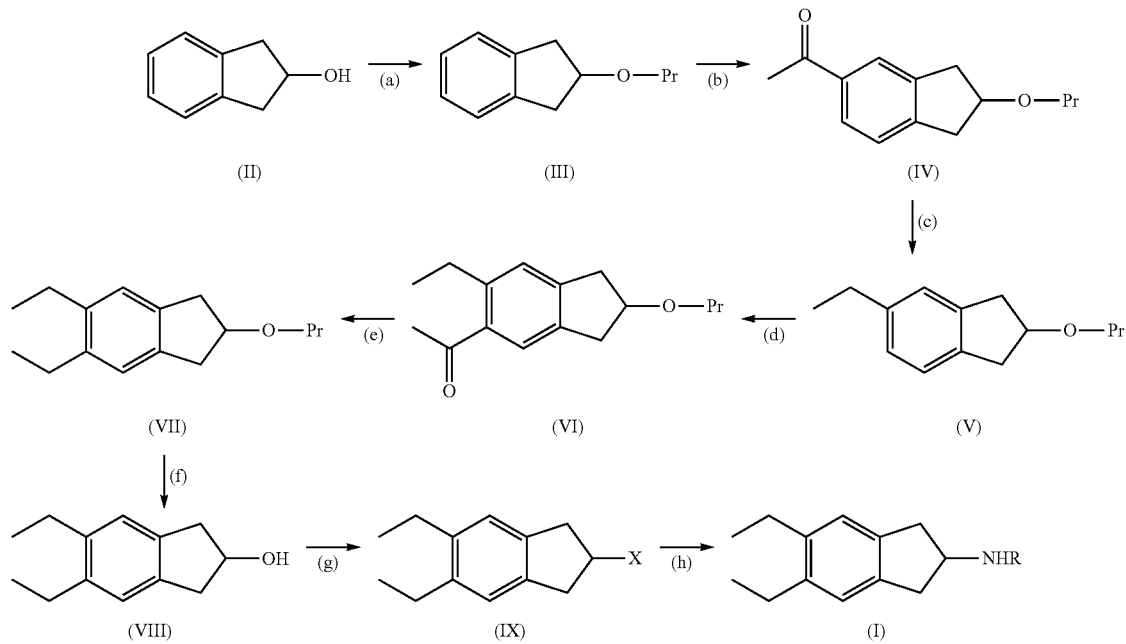

wherein R is as defined above, Pr is a protecting group of the oxygen which is not cleavable by hydrogenation and X is a leaving group for a nucleophilic substitution. In particular, it is a subject-matter of the invention a process for the preparation of a compound of formula (I)

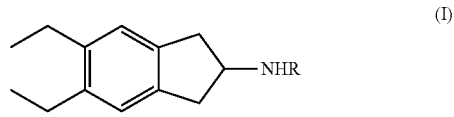

(I)

or the salts thereof, wherein R is a hydrogen atom or an amine protecting or activating group, comprising:

(a) protecting the hydroxy of the compound of formula (II) to obtain the compound of formula (III);
(b) carrying out a Friedel Crafts reaction on the compound of formula (III) to obtain the compound of formula (IV);
(c) reducing the compound of formula (IV) to obtain the compound of formula (V);
(d) carrying out a Friedel Crafts reaction on the compound of formula (V) to obtain the compound of formula (VI);
(e) reducing the compound of formula (VI) to obtain the compound of formula (VII);
(f) deprotecting the hydroxy of the compound of formula (VII) to obtain the compound of formula (VIII);
(g) introducing the X leaving group in place of the hydroxy to obtain the compound of formula (IX);
(h) reacting the compound of formula (XI) with a compound of formula R—NH$_2$ to obtain the compound of formula (I) and optionally converting it into a salt thereof.

As "protecting group of the oxygen which is not cleavable by hydrogenation" it is meant herein to denote a protecting group which is not removed by the reduction reaction of the first ketone group introduced with the Friedel-Crafts reaction. Such protecting groups include acetyl, trifluoroacetyl and benzoyl and substituted benzoyls with deactivating substituents for the Friedel-Crafts reaction.

A preferred protecting group according to the present invention is the acetyl group.

As "X leaving group for a nucleophilic substitution" it is meant herein to denote a group allowing the nucleophilic substitution on the compound (VIII). Such groups include methanesulfonate, p-toluenesulfonate, benzenesulfonate, trifluoromethanesulfonate and halogens, for example chlorine and bromine. A preferred X group according to the present invention is the methanesulfonate group (also known as mesylate group).

The "amine protecting or activating group" includes benzyl and substituted benzyl, the latter being for example substituted with electron donating groups, the unsubstituted benzyl being a preferred group.

In step (a) the hydroxy protection can be carried out according to the techniques known to one skilled in the field, advantageously with an acyl halide, for example acetyl chloride which is not expensive and easily removable. Moreover, the use of the acetyl chloride avoids the isolation of the compound of formula (III) and allows to carry out step (a) and step (b), i.e., the Friedel-Crafts reaction, as a one-pot reaction, without therefore isolating the intermediate compound.

The Friedel-Crafts reaction of step (b) is carried out in the presence of an acyl halide, advantageously acyl chloride and a Lewis acid, for example AlCl$_3$ according to the known techniques. Preferably, the acetyl-indanol/acyl halide/Lewis acid molar ratios are about 1/2-4/1.5-3.5, more preferably 1/3/2.5. The reaction temperature can range from −15° C. to +10° C., advantageously between −10° C. and +0° C., for example about −10° C.

When the reactions of steps (a) and (b) are carried out as a one-pot reaction, the acetyl-indanol/acyl halide/Lewis acid molar ratios are preferably 1/4/2.5.

The dilution of the reaction bulk in step (b) can vary from 4 to 11 volumes, preferably 4-6 volumes of solvent, with respect to the starting product. It has been unexpectedly noted that by carrying out the reaction at low temperature, for example lower than 0° C., advantageously lower than −5° C., for example about −10° C., and by reducing the amount of solvent used, it is possible to half the formation of the undesired isomers (i.e., the compounds wherein the group introduced by the Friedel-Crafts reaction is in the 3 and 6 positions). As a matter of fact it has been observed that a dilution of 4-6 volumes (with respect to the starting compound) allows to obtain an improvement in the yields of the desired compound with respect to what is obtained by using bigger solvent volumes. It can be easily understood that, in addition to a significant increase of the reaction yield, this involves also a reduced use of solvent which, from an industrial point of view, leads to a significant saving by reducing the costs of the raw material and disposal. This result is unique and unexpected.

The reduction reaction of step (c) can be carried out according to any possible known technique, for example the catalytic hydrogenation of the ketone in a suitable solvent, for example in an alcohol or in acetic acid, for example in ethanol, optionally with the addition of acetic acid, and by using Pd/C as catalyst. An example of a preferred hydrogenation of the step (c) is provided in the Experimental Section below.

In step (d), the Friedel Crafts reaction of step (b) is repeated in order to introduce the second substituent, preferably under the conditions described above.

Unless desired, it is not necessary to isolate the intermediate of formula (VI) and the following reduction reaction of step (e), advantageously carried out according to the procedures described in step (c), can be carried out on the raw product of the reaction of step (d).

The compound (VII) may also not be isolated and the deprotection reaction of step (f) can be carried out on the raw product of the reaction according to any method known in the art, for example in a solvent such as an alcohol, in a weakly basic environment. By way of example, the reaction can be carried out by heating a mixture of the raw product of the reaction of step (e) in ethanol, in the presence of an alkaline metal carbonate.

As an alternative to step (f), it is possible to carry out the hydrogenation step (e) under an acidic pH, for example in the presence of acetic acid, at temperatures of about 60-70° C. In this case, the compound of formula (VI) is reduced and deprotected at the same time, directly providing the compound of formula (VIII).

The compound (VIII) obtained from the reaction of step (e) under the above described conditions or from step (f), when carried out, may not be isolated and purified and it is possible to proceed to the reaction of step (g) directly on the raw product of the reaction.

The step (g) can be carried out according to the methods known in the art, for example from the mixture of the compound (VIII) in a suitable solvent, in a basic environment, for example by addition of an amine, such as diisopropylethylamine and by adding the desired reagent to obtain the X group. By way of example, if it is desired to obtain the compound (VIII) wherein X is a methanesulfonate, p-toluenesulfonate, benzenesulfonate, trifluoromethanesulfonate group and the like, it is possible to use a methanesulfonyl, p-toluenesulfonyl, benzenesulfonyl or trifluoromethanesulfonyl halide, the halide being preferably chloride.

Alternatively, if it is desired to obtain the compound (VIII) wherein X is a halogen atom, it will be possible to use conventional halogenating agents, including HX; therefore, in the case of chlorine, it will be possible to use a conventional chlorinating agent, such as HCl, $SOCl_2$, $PCl_3$, $PCl_5$, and the like.

According to a preferred embodiment, X is selected from methanesulfonate and p-toluenesulfonate, advantageously methanesulfonate.

The compound of formula (IX) is preferably isolated and purified according to known methods and is converted into the compound of formula (I) by reacting with the desired amine of formula $NH_2R$ in step (h). When the reaction is carried out with ammonia or benzylamine, it is preferably performed without any solvent, by simply heating the mixture of the compound of formula (IX) and of the amine.

According to a preferred embodiment, the process of the invention is carried out according to the following scheme (II):

Scheme (II)

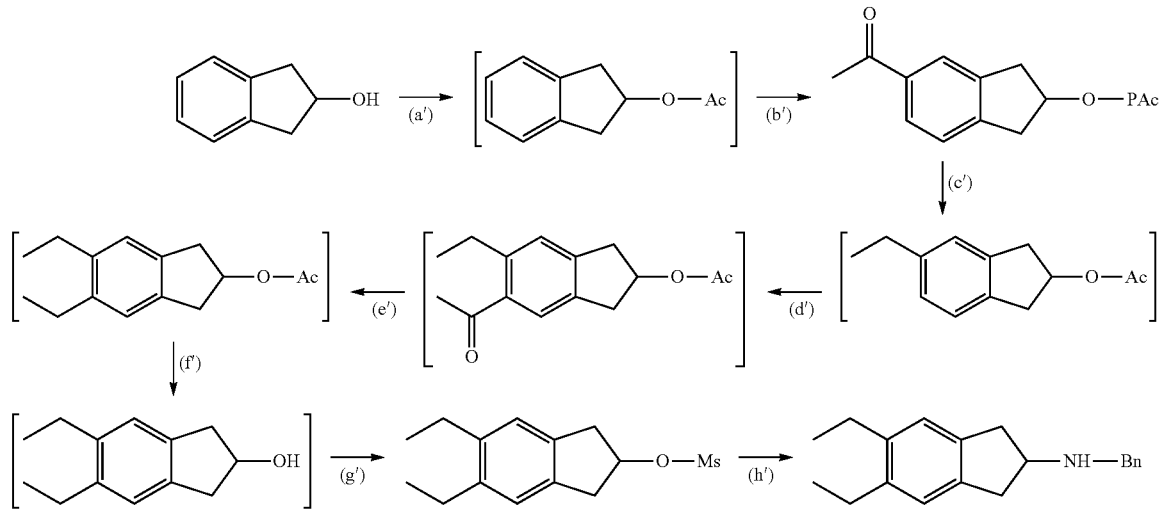

wherein
Ac=acetyl, Ms=mesyl and Bn=benzyl.

According to a particularly preferred embodiment, the process of Scheme (II) is carried out by combining together steps (a') and (b') and by carrying out the reaction of step (e') under acidic environment and at a temperature of about 60-70° C. to avoid step (f) according to the following scheme (III):

wherein Ac is an acetyl group, are new and represent a further subject-matter of the present invention.

According to a preferred embodiment, in the compound of formula (IX), X is selected from a halogen atom, a methanesulfonate group, a p-toluenesulfonate group, a benzenesulfonate group and a trifluoromethanesulfonate group.

According to a particularly preferred embodiment, X is selected from a chlorine atom, a methanesulfonate group, a Scheme (III)

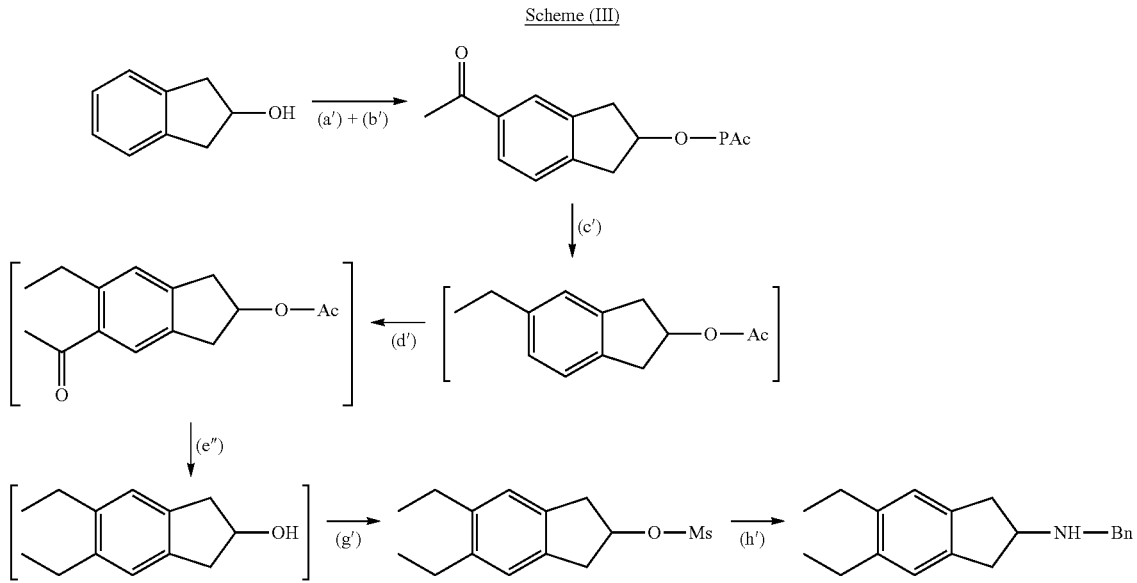

With respect to known synthesis, for example the synthesis described in WO03/076387, the process of the invention allows to obtain the compounds of formula (I) in an original and even easier way, by using the specific sequence if reactions described above which involve cheap reagents and do not require the isolation and purification of the individual intermediates. As a matter of fact, in performing the process described in WO03/076387, it is necessary to isolate and crystallize nearly all of the intermediates obtained from the various steps, whereas in the synthesis subject-matter of the invention it is necessary to isolate only the compounds (IV) and (IX) (see Scheme (I)). These further treatments significantly affect yields and industrial costs and also for these reasons the process of the invention is a technical advancement with respect to the known art.

If desired, however, such intermediates can be obviously isolated and purified.

The compounds of formula (VII), (VIII), (IX), (X) and (XI)

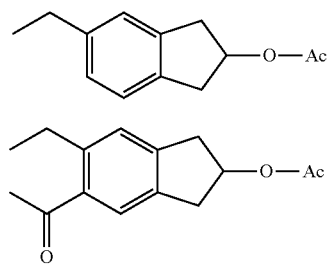

(X)

(XI)

p-toluenesulfonate group, a benzenesulfonate group and a trifluoromethanesulfonate group.

A particularly preferred compound of formula (IX) is the compound wherein X is a methanesulfonate group.

Subject-matter of the invention, according to another of the aspects thereof, is a process for the preparation of a compound of formula (VIII) comprising carrying out the reactions of steps (a) to (f) as defined above.

Subject-matter of the invention, according to another of the aspects thereof, is a process for the preparation of a compound of formula (IX) comprising carrying out the reactions of steps (a) to (g) as defined above.

If desired, it is possible to convert the compound of formula (I) into a salt thereof, for example into the hydrochloride, according to the methods known in the art.

A further subject-matter of the invention is the use of the compound of formula (I) or a salt thereof obtained by the process described herein and claimed for the preparation of the indacaterol.

It is also a subject-matter of the invention the use of at least one compound selected from the compounds of formula (VII), (VIII), (IX), (X) and (XI) as defined above for the preparation of the indacaterol.

It is a further subject-matter of the invention a process for the preparation of a compound of formula (I) as defined above, or a salt thereof, comprising:

introducing the group of formula Pr' on the hydroxy of a compound of formula (VIII)

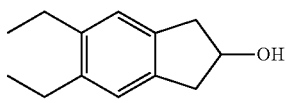

to obtain the compound of formula (IX)

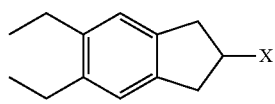

reacting the compound of formula (IX) with a compound of formula R—NH$_2$ wherein R is as defined above, to obtain the compound of formula (I) and optionally converting it into a salt thereof.

According to a preferred embodiment, in the process above X is selected from methanesulfonate, p-toluenesulfonate, benzenesulfonate and trifluoromethanesulfonate and a halogen atom, advantageously chlorine.

According to another preferred embodiment, in the process described above R is hydrogen or benzyl.

Experimental Section

Definitions

UPLC/MS ultra-performance liquid chromatography coupled to mass spectrometry detector
DIPEA diisopropylethylamine
DCM dichloromethane
iPrOAc isopropyl acetate
IPA isopropyl alcohol
CG gas chromatography Steps (a)+(b)

21.2 ml (298.32 mmols) of AcCl are charged into a flask, cooled to 0° C. and 10 g (74.58 mmols) of indanol are added during about 10 minutes. The bath is removed and left under stirring for 1 h. 24.8 g (186.45 mmols) of AlCl$_3$ are charged into a three-neck flask, 70 ml of DCM are added followed by cooling at 0° C. The indanol solution is then added dropwise into the suspension of AlCl$_3$ in DCM. It is stirred for 45 min. The control is done by UPLC/MS. The reaction is added dropwise into 200 ml of water and 35 ml of concentrated HCl, while keeping the temperature below 25° C. It is stirred for 45 minutes. The phases are separated, the aqueous phase is extracted once with 100 ml of DCM. It is washed with 100 ml of water, dried over sodium sulfate and concentrated to a small volume. Recrystallization is carried out from heptane/iPrOAc: 4/1 (50 ml).

Step (c)

50.3 g (230.5 mmols) of the raw product of the reaction obtained in the preceding reaction are dissolved in 522 g of ethanol, the hydrogenator is charged and 5 g of Pd/C are added. It is brought to 25 bars at ambient temperature. The hydrogenation is carried out until the completion of the reaction (GC control) followed by catalyst filtration on cellulose. It is concentrated under vacuum to a small volume.

Step (d)

18.22 g (133.6 mmols) of AlCl$_3$ are charged into a flask and 55 ml of DCM are added. It is cooled to 0° C. and 11.65 ml (161 mmols) of AcCl are added dropwise while keeping the temperature at 0° C. It is stirred for 15 minutes, then 11 g of the raw product of the reaction obtained in the preceding reaction (53.44 mmols) are added while keeping the temperature at 0° C. It is stirred for about 1 hour by checking the evolution by UPLC/MS. The reaction is added dropwise in 160 ml of cold water and 35 ml of concentrated HCl while keeping the temperature below 25° C. and stirring for 45 minutes. The phases are separated, the aqueous phase is extracted once with 80 ml of DCM. It is washed with 100 ml of water, dried over sodium sulfate and concentrated to a small volume.

Step (d)

12.4 g (50.35 mmols) of the raw product of the reaction obtained in the preceding reaction are dissolved in 350 ml of ethanol, the hydrogenator is charged and 1.33 g of Pd/C are added. It is brought to 50° C. and 25 bars and the hydrogenation is carried out until the completion of the reaction.

Step (f)

10.4 g (44.76 mmols) of the raw product of the reaction obtained in the preceding reaction are charged into a flask and 85 ml of methanol and 35 ml of water are added. 12.4 g (89.52 mmols) of K$_2$CO$_3$ are added and it is left under stirring overnight. The completion of the reaction is checked by means of UPLC/MS. It is diluted with 35 ml of water, extracted 2 times with 80 ml of DCM, dried over sodium sulfate and concentrated to a small volume.

Step (g)

3.508 g (18.43 mmols) of substrate are charged into a flask and 30 ml of DCM are added. It is cooled to 0° C. and 3.852 ml (22.11 mmols) of DIPEA are added dropwise. 1.570 ml (20.27 mmols) of MsCl are added dropwise and it is stirred until the completion of the reaction, which is checked by means of UPLC. It is washed with 20 ml 2M HCl, the phases are separated, the organic phase is washed with 30 ml of NaHCO$_3$ and then with 30 ml of HCl. It is dried over sodium sulfate and concentrated to a small volume. Crystallization is carried out from iPrOAc/heptane 1:10 (35 ml). Yield: 62% white solid.

Step (h)

2.285 ml (20.9 mmols) of benzylamine are charged into a flask which is heated to 80° C. 1.871 g (6.97 mmols) of the compound obtained in the step (g) are added portionwise followed by heating to 80° C. The reaction is checked by UPLC/MS. Dilution is carried out with 35 ml of DCM followed by washing with 15 ml of 5% citric acid to remove the unreacted benzylamine. The phases are separated and the organic phase is washed with 15 ml of 1M NaOH. It is anhydrified and concentrated to a small volume, it is diluted with 10 ml of acetone and 700 µl of concentrated HCl are added dropwise. The precipitate is filtered over a Buchner filter. 1.7 g of a white solid are obtained (Molar yield=80%). The product can be crystallized, for example in IPA, for further purification. The product contains less than 0.7-0.2% (GC analysis) of regioisomer.

Overall yield from (a) to (h) 50%.

The invention claimed is:
1. A process for the preparation of a compound of formula (I)

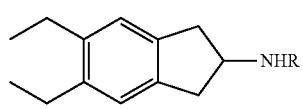

or salts thereof, wherein R is a hydrogen atom or an amine protecting or activating group, comprising:

(a) protecting the hydroxy of the compound of formula (II)

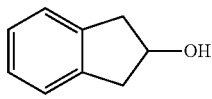
(II)

to obtain the compound of formula (III)

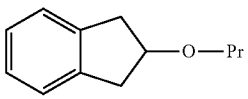
(III)

(b) carrying out a Friedel Crafts reaction on the compound of formula (III) to obtain the compound of formula (IV)

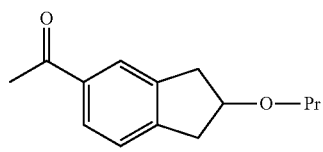
(IV)

(c) hydrogenating the compound of formula (IV) to obtain the compound of formula (V)

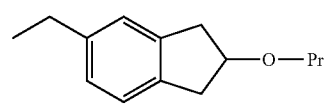
(V)

(d) carrying out a Friedel Crafts reaction on the compound of formula (V) to obtain the compound of formula (VI)

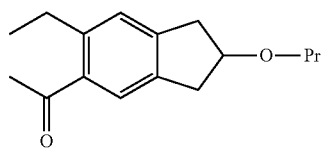
(VI)

(e) hydrogenating the compound of formula (VI) to obtain the compound of formula (VII)

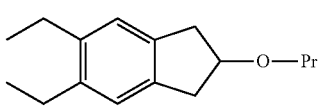
(VII)

(f) deprotecting the hydroxy of the compound of formula (VII) to obtain the compound of formula (VIII)

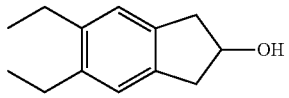
(VIII)

(g) introducing the group of formula X to obtain the compound of formula (IX);

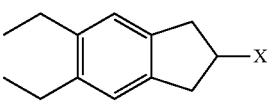
(IX)

(h) reacting the compound of formula (IX) with a compound of formula R—NH$_2$ to obtain the compound of formula (I) and optionally converting it into a salt thereof, wherein R is as defined above, Pr is a protecting group of the oxygen which is not cleavable by hydrogenation and X is a leaving group for a nucleophilic substitution.

2. The process according to claim 1, wherein Pr is selected from the group consisting of acetate, trifluoroacetate and benzoate.

3. The process according to claim 1, wherein X is selected from
the group consisting from methanesulfonate, p-toluenesulfonate, benzenesulfonate, trifluoromethanesulfonate, and a halogen atom.

4. The process according to claim 1, wherein steps (a) and (b) are carried out with an acyl halide and are performed in a one-pot reaction.

5. The process according to claim 1, wherein step (c) and step (e) are carried out by hydrogenation, in the presence of a solvent and of a catalyst.

6. The process according to claim 1, wherein step (f) is not performed and in step (e) the ketone is reduced and at the same time the hydroxy group is deprotected, to directly obtain the compound of formula (VIII).

7. The process according to claim 1, wherein in step (g) a mesyl or tosyl halide or a chlorinating agent is used.

8. The process according to claim 1, wherein in step (h) a compound of formula R—NH$_2$ is used.

9. The process according to claim 1, wherein steps (b) and (d) are carried out at temperatures lower than zero and with dilutions of 4-6 volumes of solvent with respect to the starting compound.

10. A process for the preparation of a compound of formula (VIII)

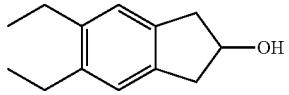
(VIII)

comprising carrying out the reactions of steps (a) to (f) as defined in claim 1.

11. A process for the preparation of a compound of formula (IX)

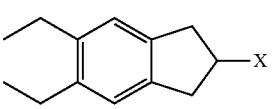
(IX)

wherein X is a leaving group comprising carrying out the reactions of steps (a) to (g) as defined in claim 1.

12. The process according to claim 11, wherein X is a methanesulfonate group.

13. A process for the preparation of a compound of formula (I)

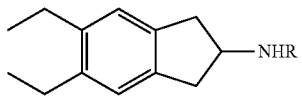
(I)

wherein R is a hydrogen atom or an amine protecting or activating group, or a salt thereof, comprising:
introducing the group of formula X on the hydroxy of a compound of formula (VIII)

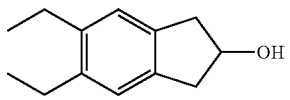
(VIII)

wherein X is a leaving group, to obtain the compound of formula (IX);

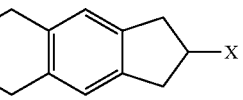
(IX)

reacting the compound of formula (IX) with a compound of formula R—NH$_2$ to obtain the compound of formula (I) and optionally converting it into a salt thereof.

14. The process according to claim 13, wherein X is selected from the group consisting of a methanesulfonate, p-toluenesulfonate, benzenesulfonate, trifluoromethanesulfonate group and a chlorine atom.

15. The process according to claim 13, wherein R is selected from the group consisting of hydrogen and benzyl.

16. The process according to claim 13, wherein X is selected from the group consisting of methanesulfonate, p-toluenesulfonate, benzenesulfonate, trifluoromethanesulfonate, and a halogen atom.

* * * * *